(12) United States Patent
Shu

(10) Patent No.: US 9,220,676 B2
(45) Date of Patent: Dec. 29, 2015

(54) INJECTABLE IN-SITU CROSSLINKED HYDROGEL AND METHODS OF MAKING AND USING THEREOF

(75) Inventor: Xiaozheng Shu, Shanghai (CN)

(73) Assignee: Bioregen Biomedical (Changzhou) Co., Ltd., Jiangsu (CN)

( * ) Notice: Subject to any disclaimer, the term of this patent is extended or adjusted under 35 U.S.C. 154(b) by 183 days.

(21) Appl. No.: 13/124,412

(22) PCT Filed: Sep. 8, 2009

(86) PCT No.: PCT/CN2009/001013
§ 371 (c)(1),
(2), (4) Date: Apr. 15, 2011

(87) PCT Pub. No.: WO2010/043106
PCT Pub. Date: Apr. 22, 2010

(65) Prior Publication Data
US 2012/0034271 A1    Feb. 9, 2012

(30) Foreign Application Priority Data
Oct. 16, 2008    (CN) .......................... 2008 1 0043845

(51) Int. Cl.
*A61K 31/56*    (2006.01)
*A61P 35/00*    (2006.01)
*A61P 31/00*    (2006.01)
*A61K 9/00*    (2006.01)
*A61L 27/52*    (2006.01)
*A61L 27/54*    (2006.01)
*A61L 31/14*    (2006.01)
*A61L 31/16*    (2006.01)
*C08J 3/075*    (2006.01)
*C08J 3/24*    (2006.01)

(52) U.S. Cl.
CPC ............ *A61K 9/0019* (2013.01); *A61K 9/0024* (2013.01); *A61L 27/52* (2013.01); *A61L 27/54* (2013.01); *A61L 31/145* (2013.01); *A61L 31/16* (2013.01); *C08J 3/075* (2013.01); *C08J 3/24* (2013.01); *A61L 2300/406* (2013.01); *A61L 2300/416* (2013.01); *C08J 2305/00* (2013.01)

(58) Field of Classification Search
None
See application file for complete search history.

(56) References Cited

U.S. PATENT DOCUMENTS

| | | | |
|---|---|---|---|
| 4,582,865 | A | 4/1986 | Balazs et al. |
| 4,713,448 | A | 12/1987 | Balazs et al. |
| 6,624,245 | B2 | 9/2003 | Wallace et al. |
| 6,884,788 | B2 | 4/2005 | Bulpitt et al. |
| 7,196,180 | B2 | 3/2007 | Aeschlimann et al. |
| 2005/0176620 | A1* | 8/2005 | Prestwich et al. ............ 514/2 |
| 2006/0147483 | A1* | 7/2006 | Chaouk et al. ............ 424/400 |
| 2006/0147783 | A1* | 7/2006 | Cho et al. .................. 429/34 |
| 2007/0269488 | A1 | 11/2007 | Ravi |

FOREIGN PATENT DOCUMENTS

| | | |
|---|---|---|
| CN | 101190891 | 6/2008 |
| CN | 101200504 | 6/2008 |
| EP | 0185070 | 6/1986 |
| WO | 86/00079 | 1/1986 |
| WO | 2004037164 | 5/2004 |
| WO | 2005056608 | 6/2005 |
| WO | WO 2006034128 A2 * | 3/2006 |
| WO | 2006113407 A2 | 10/2006 |
| WO | 2008098019 | 8/2008 |

OTHER PUBLICATIONS

Xiao Zheng Shu, Yanchun Liu, Yi Luo, Meredith C. Roberts, and Glenn D. Prestwich. Disulfide Cross-Linked Hyaluronan Hydrogels. Biomacromolecules 2002, 3, 1304-1311.*
Silva et al, Curr Top Dev Biol, 64, 181, 2004.
Drury et al., Biomaterials, 24, 4337, 2003.
Kujawa et al, Develop Biol., 114, 519, 1986.
Capozzi, G.; Modena, G.; In the Chemistry of the Thiol Group Part II; Patai S. Ed.; Wiley: New York 1974; pp. 785-839.
Shu et al, Biomacromolecules, 3, 1304, 2002.
Shu et al, Biomaterials, 24, 3825, 2003.
Liu et al, Journal of Biomedical Materials Research, 68, 142, 2004.
Gianolio et al, Bioconjugate Chemical, 16, 1512, 2005.
Benesch et al, Proc Natl Acad Sci USA, 44, 848, 1958.
Yamauchi et al, Biosubstances, 22, 855, 2001.

(Continued)

Primary Examiner — Frederick Krass
Assistant Examiner — Michael P Cohen
(74) Attorney, Agent, or Firm — MKG, LLC

(57) ABSTRACT

The present invention discloses an injectable in-situ crosslinked hydrogel and its preparation method. The preparation method is as below: Filling the crosslinking active solution of at least one kind of the biocompatible macromolecules containing more than two thiol groups on the side chains into an injectable container and sealing it, and forming the in-situ disulfide-bond crosslinked hydrogel under the action of the dissolved oxygen; through controlling such parameters as partial pressure of oxygen gas, temperature and time, regulating concentration of the oxygen dissolved in the crosslinking active solution, and optimizing the gelation process and the gel properties. The present invention further relates to application of the injectable in-situ crosslinked hydrogel in pharmaceutics or surgery. The present invention has many advantages, such as no need for a crosslinking agent, simple preparation process, convenient application, containing no impurities, good biocompatibility, no toxic and side effect, and wide application in the medical science.

21 Claims, No Drawings

(56) References Cited

OTHER PUBLICATIONS

Nicolas et al, Biosubstances, 8, 807, 1997.
Kafedjiiski et al, Biosubstances, 26, 819, 2005.
Ossipov et al, Maxromolecules, 41, 3971, 2008.
Lutolf et al, Nature Biotechnology, 23, 47, 2005.
Kirker et al, Biosubstances, 23, 3661, 2002.
Bernkop-Schnurch, Andreas, Thiomers: A new generation of mucoadhesive polymers, Elsevier, Advanced Drug Delivery Reviews 57 (2005) 1569-1582, available online Sep. 19, 2005.
Hansen, J. Norman, Electrophoresis of ribonucleic acid on a ployacrylamide gel which contains disulfide cross-linkages, Biochemistry Division of the Department of Chemistry, University of Maryland, accepted Jun. 18, 1976.
Lozinskii, V. I., et al., Change in the amount of Titrated SH groups in the polyacrylamide thiol derivative during freezing of its aqueous solutions, Polymer Science U.S.S.R., vol. 31, No. 2, pp. 367-372, 1989.
Swindle, Katelyn, E., et al., In situ formation of hydrogels as vitreous substitutes: Viscoelastic comparison to porcine vitreous, Journal of Biomedical Materials Research Part A, published online Jan. 11, 2008 in Wiley Inter-Science.

* cited by examiner

INJECTABLE IN-SITU CROSSLINKED HYDROGEL AND METHODS OF MAKING AND USING THEREOF

FIELD OF THE INVENTION

The present invention relates to a hydrogel, and particularly to an injectable in-situ disulfide-bond crosslinked hydrogel. Furthermore, the present invention relates to its preparation methods and use in medicine or surgical operations.

BACKGROUND OF THE INVENTION

Hydrogel is the most common and important substance with high water content but insoluble in water. It can absorb water in amounts up to several hundredfold over its own weight while still keeping its shape. Natural gels existing inside of most organisms and plants, and many chemically synthesized gels belong to hydrogels. Macromolecular gels are a kind of common hydrogel. They have a three-dimensional crosslinked network structure composed of the main chains of macromolecules and also side chains containing hydrophilic (polar) groups, hydrophobic groups and/or dissociable groups with the solvent entrapped in the molecular network. The crosslinked sites of the macromolecular gel network can be either formed by chemical-crosslinking through covalent bonds, or formed by physical-crosslinking through electrostatic interaction, hydrogen-bond interaction, hydrophobic interaction, etc.

Hydrogels, especially the macromolecular hydrogels prepared with the extracellular matrix materials, are widely used in the field of biomedicine. Compared with the hydrogels prepared with synthetic materials, the hydrogels prepared with the extracellular matrix have many advantages, such as simulating the natural environment as the inside of organisms, very high water content, good permeability, better biocompatibility, and adjustable enzymatic degradability. More importantly, the extracellular matrix may possess bioinduction functions, can direct and induce specific regeneration of tissues. For example, sodium hyaluronate is a natural extracellular matrix macromolecule, possessing biological functions such as managing cell adhesion and migration, and regulating cell division and differentiation. The high molecular weight sodium hyaluronate can induce a chicken embryonic limb marrow stem cell to be differentiated into a cartilage cell. Therefore, in the biomedicine (particularly the tissue engineering) field more and more attention is focused on the hydrogel prepared with extracellular matrix.

Although hydrogels have a number of advantages, the method of administration significantly limits its wide application in the biomedicine field. Currently many medical products of hydrogels are formulated into films and porous sponges etc., e.g. gelatin sponge and collagen sponge. Usually these products can only be used topically or in laparotomy. However, with the development of the medical technology, more and more doctors and patients are inclined to the minimally invasive surgery, requesting that the medical products can also be used under endoscopes, which present a new challenge for developing medical products.

The injectable hydrogel medical products can be used either under an endoscope or in combination with a minimally invasive surgery. They are also suitable for three-dimensional wounds of any complicated shape, and can adhere to the wounds very well, having prospects of wide application in the biomedicine field. For example, currently as the new-generation anti-wrinkle fillers, various injectable crosslinked hydrogels made from sodium hyaluronate that overcome the immunogenicity risk of the collagen anti-wrinkle filler, have been widely used in cosmetology. As representative products of such new-generation anti-wrinkle fillers, Restylane (Q-Med, Sweden), Hylaform (Inamed Corporation, the United States), Juvederm (Leaderm, France), Belotero (Anteis, Switzerland), and Puragen (Mentor Corporation, the United States) are commercially available in Europe (among them Restylane and Hylaforms have further been approved by the FDA of the United States).

Currently, most medical products of hydrogels are prepared by chemical crosslinking followed by purification to remove residual crosslinking agents and byproducts. However, the chemical crosslinking agents usually have great toxic and side effects, and even a complicated process can hardly guarantee to remove them completely. More seriously, the residual crosslinking agents with part of functional groups crosslinked, have been immobilized in the hydrogel via covalent bonds, and cannot be removed. These residual crosslinking agents may cause toxicity and side effects such as inflammation in clinicals. For example, trace amounts of residual crosslinking agents in the gelatin sponge may cause a serious inflammation response in organisms. The previously described injectable crosslinked hydrogels made from sodium hyaluronate are also prepared by the process of crosslinking first and then purification. For example, Restylane and Hylaforms have been prepared by chemical reactions between the hydroxyl group of sodium hyaluronate and 1,4-tetramethylene glycol diglycidyl ether or divinyl sulfoxide. However, the residual 1,4-tetramethylene glycol diglycidyl ether or divinyl sulfoxide are very difficult to remove completely from the hydrogel, and those with one function group being reacted and fixed in the hydrogel via the covalent bond cannot be removed. This limitation not only requires a complicated purifying process, but also raises clinical risks.

Recently, disulfide-bond crosslinked hydrogels have been investigated. This disulfide bond is a reversible chemical bond, free thiol groups can be oxidized into disulfide bonds which can be reduced back into free thiol groups. For example, currently the disulfide-bond crosslinked hydrogel has been used as a cell culture matrix, and the cells can be recovered very conveniently by adding cell-compatible reducer of disulfide bonds.

Oxidants (i.e. hydrogen peroxide, iodine, alkyl peroxide, acid peroxide, dimethyl sulfoxide, $Fe^{3+}$, $Co^{3+}$, $Ce^{4+}$, etc.) can oxidize thiol groups into disulfide bonds. However, these oxidants usually have certain toxic and side effects, and are highly harmful if left in the medical products; moreover their oxidation capacity is too strong, and the reaction is so vigorous that the disulfide bond will be further oxidize into byproducts such as sulfonate.

Oxygen can also oxidize free thiol groups into disulfide bonds. One oxygen gas molecule can oxidize four thiol groups into two disulfide bonds, and produce two water molecules as well, without any other byproducts. Preparing disulfide-bond crosslinked hydrogels with oxygen gas as the oxidant has many advantages, such as simple and mild reaction conditions and no need for a crosslinking agent. By using oxygen gas as the crosslinking agent to prepare disulfide-bond crosslinked hydrogels, it is hopeful to break the limitation of the residual crosslinking agent in the hydrogel preparation process as described above.

Disulfide-bond crosslinked hydrogels have many potential applications in the biomedicine field, and have been paid much attention in recent years. So far, however, there has been no report about their practical clinical applications, and two major reasons are responsible for that. The first is that the current preparation process of the disulfide-bond crosslinked hydrogel is not suitable for industrialized production. Using oxygen gas to oxidize the thiol group into the disulfide-bond crosslinked hydrogel under physiological conditions is a slow process, which needs to continuously consume a lot of oxygen. It is widely accepted by those skilled in the art that making the solution open to air is a precondition for forming the disulfide-bond crosslinked gel. In the current disclosed reports, all the biocompatible macromolecule solutions containing thiol groups need to be open to air for forming the disulfide-bond crosslinked gel. For example, thiolated sodium hyaluronate derivative solution can form the disulfide-bond crosslinked gel when being open to air, and produce a disulfide-bond crosslinked film after being dried; the mixed solution of thiolated sodium hyaluronate derivative and thiolated collagen derivative can form the disulfide-bond crosslinked gel when being open to air, and produce the disulfide-bond crosslinked film or porous sponge after being dried at the normal or freezing temperatures. The second for preventing the disulfide-bond crosslinked hydrogel from being used in the clinical practice is the product form. Most of the disulfide-bond crosslinked gels currently reported are prepared in the form of film or sponge, and can only be used topically or in laparotomy, not meeting the requirements of many clinical therapies (especially the minimally invasive surgery).

So far there has been a widespread technical prejudice among those skilled in the art: The biocompatible macromolecule solution containing the thiol group needs to be open to air for forming the disulfide-bond crosslinked hydrogel. To a great extent, this prejudice limits the large-scale industrialized production process of the disulfide-bond crosslinked hydrogel. So far there has been no report about preparing the disulfide-bond crosslinked hydrogel in a sealed injectable container, although this injectable disulfide-bond crosslinked hydrogel has very wide application in the biomedicine field.

SUMMARY OF THE INVENTION

The present invention resides in one aspect in providing an injectable in-situ disulfide-bond crosslinked hydrogel, whose gelation process is completed in a syringe. This injectable in-situ disulfide-bond crosslinked hydrogel is injectable, convenient to use, free of impurities, and good biocompatibility, and has no toxic and side effects, having prospects of very wide application in the biomedicine field.

A second purpose of the present invention is to provide a method of preparing the injectable in-situ disulfide-bond crosslinked hydrogel. This method eliminates the technical prejudice that being open to air is required for preparing the disulfide-bond crosslinked hydrogel, resolves the technical problem with the large-scale industrialized production, and simplifies the preparation process.

A third purpose of the present invention is to apply the injectable in-situ disulfide-bond crosslinked hydrogel in pharmaceutics or surgery.

On one hand, the present invention provides a method of preparing the injectable in-situ disulfide-bond crosslinked hydrogel, which includes the following steps:

(1) Filling a crosslinking active solution into an injectable container, wherein the crosslinking active solution containing at least one kind of the biocompatible macromolecules with more than two thiol groups on the side chain;

(2) Sealing the injectable container containing the crosslinking active solution; and (3) Oxidizing the thiol groups into the disulfide bonds to form the crosslinked hydrogel by the oxygen dissolved in the crosslinking active solution in the sealed injectable container.

The thiol group is oxidized in a sealed injectable container into the in-situ disulfide-bond crosslinked hydrogel by the oxygen dissolved in the crosslinking active solution. Besides, this method can flexibly regulate concentration of the oxygen dissolved in the crosslinking active solution by conveniently controlling such parameters as temperature, partial pressure of oxygen gas, or contact time, thus regulating the disulfide bond crosslinking process and properties of the disulfide-bond crosslinked hydrogel.

Some of the terms used in the present invention are defined as below.

"Hydrogel" refers to a substance with a three-dimensional crosslinked network structure containing a great deal of water, with the state between a liquid and a solid without fluidity. "Gelation" refers to a process by which a liquid with fluidity is changed into a gel without fluidity; and "gelation time" refers to a time period during which a liquid with fluidity is changed into a gel without fluidity.

In the present invention, "crosslinking active solution" refers to a solution containing at least one kind of the biocompatible macromolecules with more than two thiol groups on the side chain. The crosslinking active solution uses water as the main solvent, and can also contain some salt components (e.g. sodium chloride and pH buffer salt) for regulating osmotic pressure and stabilizing pH value of the solution, etc.; besides, the crosslinking active solution may also contain some other polar, water-soluble components, such as ethanol.

In the present invention, "biocompatible macromolecule with more than two thiol groups on the side chain" mainly refers to the derivative produced by one or more chemical modifications of polysaccharides, proteins or synthetic macromolecules, wherein at least one of the chemical modifications is the thiol modification.

Polysaccharides include chondroitin sulfate, heparin, heparan, alginic acid, hyaluronic acid, dermatan, dermatan sulfate, pectin, carboxymethyl cellulose, chitosan, and so on as well as their salt forms (such as sodium salt and potassium salt). The proteins include collagen, alkaline gelatin, acidic gelatin, gene recombination gelatin, and so on. The synthetic macromolecules include polyacrylic acid, polyaspartic acid, polytartaric acid, polyglutamic acid, polyfumaric acid, and so on as well as their salt forms (such as sodium salt and potassium salt). The chondroitin sulfate as described above includes such various types as Type A, Type B, and Type C. Molecular weights of the polysaccharides, the proteins and the synthetic macromolecules are usually in the range of 1,000-10,000,000. The synthetic macromolecules as described above do not include polyethylene glycol.

The chemical modification method includes hydrophobization modification (e.g. alkylation modification), carboxylation modification (e.g. carboxymethylation modification), thiol modification and so on.

The thiol modification refers to a chemical modification process of introducing free thiol groups. Usually, the free thiol groups can be introduced via the functional groups on side chains (such as carboxyl group, amino group, and hydroxyl group) of polysaccharides, proteins and synthetic macromolecules through appropriate chemical reactions. A common thiol modification mainly includes the following chemical reaction processes: Reacting of the side chain carboxyl groups of polysaccharides, proteins and synthetic macromolecules with diamines or dihydrazides containing the disulfide bonds under activation of carbodiimides to produce the intermediate products, and then reducing the disulfide bonds into the free thiol groups. Primary amines with protected thiol groups are also can be used in place of the diamines or dihydrazides containing the disulfide bonds. Many polysaccharides, proteins, and synthetic macromolecules containing carboxyl groups on the side chain can be processed in this way to produce the derivatives with more than two thiol groups on the side chain, e.g. thiolated sodium hyaluronate derivatives, thiolated chondroitin sulfate derivatives, thiolated gelatin derivatives. The derivatives containing more than two thiol groups on the side chain can also be produced through direct reaction of the carboxyl groups with the carbodiimides containing the disulfide bonds (e.g. 2,2'-dithiobis-(N-ethyl(N'-ethylcarbodiimide))) following reduction of the disulfide bonds.

Another common thiol modification is direct or indirect chemical modifications of the side chain amino groups of polysaccharides, proteins and synthetic macromolecules. For example, the thiol modification can be realized by the reaction of the side chain amino group of such proteins as collagen with an activation substance containing the disulfide bond (e.g. the activated disuccinic bisacylcystamine dicarbonyl diimidazole ester), and the reduction of the disulfide bond into the free thiol group. The thiol modification of the side chain amino group of polysaccharides, proteins and synthetic macromolecules can also be realized indirectly, for example, first carboxylizing the amino group, and then realizing the thiol modification by means of the carboxyl group modification.

Thiol modification of the side chain hydroxyl group of polysaccharides, proteins and synthetic macromolecules is also commonly used. For example, the side chain hydroxyl group of such polysaccharides as cellulose, hyaluronic acid, chitin and chitosan can be carboxylized under strong alkaline conditions, and then the carboxyl group is thiolated by the above method. Carbylan-S is just such a sodium hyaluronate thiolated derivative prepared in this way. The side chain hydroxyl group can also be thiolated through a direct chemical reaction, such as the polyvinyl alcohol thiolated derivative.

In the present invention, the biocompatible macromolecule containing more than two thiol groups on the side chain can also be prepared through such methods as the fermentation of gene engineering. In the gene engineering, the biocompatible macromolecule containing more than two thiol groups on the side chain can be produced through the fermentation engineering by controlling the expression of the gene fragment according to the theoretically defined molecular structure.

In the present invention, the derivatives containing more than two thiol groups on the side chain can be prepared conveniently into the injectable gel according to the present invention, such as thiolated sodium hyaluronate derivatives, thiolated chondroitin sulfate derivatives, thiolated heparin derivatives, thiolated chitosan derivatives, thiolated gelatine derivatives, and thiolated collagen derivatives.

In the present invention, the crosslinking active solution can contain either one kind or two or more kinds of the biocompatible macromolecules containing more than two thiol groups on the side chain. For example, as required by different applications, the crosslinking active solution can contain one kind or multiple kinds of following substances: thiolated sodium hyaluronate derivatives, thiolated chondroitin sulfate derivatives, thiolated heparin derivatives, thiolated gelatine derivatives, thiolated collagen derivatives, and thiolated chitosan derivatives.

In the present invention, besides at least one kind of the biocompatible macromolecules having more than two thiol groups on the side chain, the crosslinking active solution can further contain one kind or multiple kinds of other substances. These substances can be polysaccharides, proteins or macromolecule compounds, such as sodium hyaluronate, chondroitin sulfate, parin sodium, acidic gelatin, alkaline gelatin, gene recombination gelatin, polyacrylic acid, polyaspartic acid, polytartaric acid, polyglutamic acid, polyfumaric acid, and so on; these substances can also be active medical components, including steroids, antibiotics, and antitumor drugs, such as various protein drugs, e.g. various growth factors (a basic growth factor, an acidic growth factor, a blood vessel growth factor, an ossification growth factor, etc.), and nucleic acids (e.g. RNA); besides, these substances can be various small molecular drugs (e.g. antibiotics and corticosteroids) and so on. This active medical component can be either dispersed in the crosslinking active solution in a solid particle form, or dissolved in the crosslinking active solution.

The thiol group, as a functional group naturally existing in an organism and possessing good biocompatibility, has very good reactivity. The disulfide bond is a reversible chemical bond. The free thiol group can be oxidized into the disulfide bond, which can be reduced back into the free thiol group. This is important for biology. The disulfide-bond crosslinked hydrogel has prospects of important application in the bio-medicine field; for example, it can be used for promoting wound healing, as a cell culture carrier, and for tissue repair and regeneration.

Oxygen gas, as a natural moderate biocompatible oxidant, widely exists in various physiological processes inside the human body. Oxygen gas can also oxidize the free thiol group into the disulfide bond. One oxygen gas molecule can oxidize four thiol groups into two disulfide bonds, and produce two water molecules as well, without any other byproducts. The present invention, with oxygen gas as the oxidant, is advantageous in many aspects, such as simple and mild reaction conditions, and no need for crosslinking agents.

For the disulfide-bond crosslinked hydrogel with oxygen gas as the oxidant, there is a widespread technical prejudice among those skilled in the art: The biocompatible macromolecule solution containing the thiol group needs to be open to air for forming the disulfide-bond crosslinked hydrogel. We made a deep research on the disulfide-bond crosslinking gelation process. The result indicates that it is mainly the oxygen dissolved in solution instead of the oxygen gas in air that oxidizes the thiol group into the crosslinked disulfide bond. This discovery provides a new approach for preparing the disulfide-bond crosslinked hydrogel, and indicates the possibility of the large-scale industrialized production process.

So far there has been no research reports about preparing the disulfide-bond crosslinked hydrogel by means of the oxygen dissolved in solution under sealed conditions. The research results as described above indicate a new approach for us: The crosslinking active solution may also form the disulfide-bond crosslinked hydrogel under isolation conditions from air, and the key point is the content of the oxygen dissolved in the crosslinking active solution. For example, it is indicated by our research that the neutral solution of 1.0% (w/v) thiolated sodium hyaluronate derivative (with 45% carboxyl groups modificated into the thiol groups) is isolated from air after being filled into an syringe, and will usually lose fluidity gradually in 2-7 days to form the disulfide-bond crosslinked hydrogel.

It is revealed by further analysis that the content of thiol groups in the neutral solution of 1.0% (w/v) thiolated sodium hyaluronate derivative in the above example is about 10 mmol/L (i.e. 330 mg/L), which correspondingly needs 2.5 mmol/L (namely 80 mg/L) dissolved oxygen gas to oxidize all the thiol groups into the disulfide bonds. The saturated solubility of oxygen gas in water is only 8.4 mg/L (25° C.) at the normal temperature of 25° C., which can theoretically only oxidize 10% free thiol groups in the thiolated sodium hyaluronate derivative solution described above into the disulfide bonds. Although the concentration of the dissolved oxygen is usually lower than the saturated solubility in the actual process, the dissolved oxygen is also enough to form the disulfide-bond crosslinked hydrogel under sealed conditions, but the hydrogel is lower in strength and the gelation time is longer.

In order to further regulate the gelation process and the gel property (e.g. strength), the concentration of the oxygen dissolved in the crosslinking active solution is regulated as one of the important means of the present invention. Generally, the saturated solubility of oxygen gas in water can be calculated according to the Henry's law ($C_{O2}=K_{O2}P_{O2}$), where $C_{O2}$ is the saturated solubility of oxygen gas in water, $K_{O2}$ the Henry's constant, and $P_{O2}$ the partial pressure of oxygen gas.

At 1 atm, for example, the solubility of oxygen gas in water saturated with air can be calculated according to the Henry's law. With the partial pressure of water vapor at 25° C. being 0.0313 atm and there being 20.95% oxygen gas in dry air, the partial pressure of oxygen gas according to the Dalton partial pressure law is $P_{O2}$=(1.0000 atm−0.0313 atm)× 0.2095=0.2029 atm; the Henry's constant of oxygen gas in 25° C. water is $K_{O2}$=1.28×10$^{-8}$ mol/(L·Pa). Therefore, the solubility of oxygen gas in water according to the Henry's law is $C_{O2}=K_{O2} \cdot P_{O2}$=1.28×10$^{-8}$×0.2029×1.013×10$^5$=2.63×10$^{-4}$ mol/L; with the molecular weight of oxygen gas being 32, the saturated solubility of oxygen gas is 8.4 mg/L.

Temperature is an important factor affecting the solubility of oxygen gas in water, which can be expressed by the Clausius-Clapeyron equation as $$\log\frac{c_1}{c_2} = \frac{\Delta H}{2.303R}\left[\frac{1}{T_1} - \frac{1}{T_2}\right],$$

where $C_1$ and $C_2$ are saturated solubility of the gas in water (mg/L) at absolute temperatures $T_1$ and $T_2$, respectively; $\Delta H$ is the heat of dissolution (J/moL); and R is the gas constant (8.314 J/K·moL). It can be seen from the above formula that the saturated solubility of oxygen gas in water decreases gradually with the increasing temperature. For example, when the temperature goes up from 4° C. to 25° C., concentration of the oxygen saturatedly dissolved in pure water is decreased from 13.1 mg/L to 8.4 mg/L.

Pressure is a key factor affecting the solubility of oxygen gas in water. According to the Henry's law $C_{O2}=K_{O2} \cdot P_{O2}$, the saturated solubility of oxygen gas in water is in direct proportion to the partial pressure of oxygen gas at certain temperatures. At 25° C., for example, the solubility of oxygen gas in water saturated with air (1 atm) is 8.4 mg/L, while the solubility in water saturated with oxygen gas (1 atm) is increased by about 5 times (about 40 mg/L).

The salt content in water will also affect the saturated solubility of oxygen gas in water, although not so significantly. The solubility of oxygen in water will decrease with the increasing salt content. For example, concentration of the oxygen saturatedly dissolved in seawater is generally about 80% as much as that in fresh water.

In the present invention, concentration of the oxygen dissolved in the crosslinking active solution is usually regulated by controlling partial pressure of oxygen gas and temperature. Concentration of the oxygen saturatedly dissolved can be increased by decreasing temperature, with the temperature commonly in the range of 0-50° C., most commonly 4-40° C. The partial pressure of oxygen gas is the most important factor for regulating concentration of the oxygen dissolved in the crosslinking active solution. According to the Henry's law, the saturated solubility of oxygen gas in water is in direct proportion to the partial pressure of oxygen gas under the same conditions. By regulating the partial pressure of oxygen gas, concentration of the oxygen dissolved in the crosslinking active solution can then be regulated conveniently, thus the gelation process of the free thiol group oxidized into the disulfide bond being regulated. At 25° C., for example, the saturated concentration of oxygen dissolved in water is 8.4 mg/L under 1 atm air, and will be increased by about 5 times (40 mg/L) under 1 atm oxygen gas, equivalent to the concentration of the oxygen saturatedly dissolved under 5 atm air; and vacuum pumping for 15 minutes can then remove almost all the oxygen dissolved in water. In the present invention, increasing the concentration of the oxygen dissolved in the crosslinking active solution can significantly expedite the gelation process and increase the strength of the gel, and will otherwise retard the gelation process and decrease the strength of the gel.

The preparation method of the present invention usually includes the following steps:

(1) Filling the crosslinking active solution into an injectable container;

(2) Sealing the injectable container containing the crosslinking active solution; and (3) Oxidizing the thiol group into the disulfide bond by the oxygen dissolved in the crosslinking active solution to form the crosslinked hydrogel.

The present invention can be realized through the sterile process or the terminal sterilization process, so as to meet different medical requirements. Usually the crosslinking active solution can be filled into an injectable container manually or by means of a filling equipment in the medical industry, and then the in-situ disulfide bonds in the injectable container are crosslinked to form the gel.

The present invention eliminates the technical prejudice that being open to air is required for preparing the disulfide-bond crosslinked hydrogel, and solves the technical problems with the large-scale industrialized production of the injectable disulfide-bond crosslinked gel. With the preparation method of the present invention, the large-scale industrialized production can then be realized with the filling production line commonly used in the medical industry, with the hourly output easily up to more than 3000 pieces. The filling production line can be selected from a straight line full-automatic syringe prefilling production line or a beehive syringe full-automatic prefilling and sealing equipment manufactured by the Groninger company, and a presterilization syringe liquid prefilling and sealing machine manufactured by the Bosch company of Germany, etc. The injectable container can be made of either glass or plastic, such as the Hypac SCF presterilization syringe manufactured by the BD company. The syringe can also be replaced by such extrusible containers as soft plastic bags.

The steps (1) and (2) as described above can be realized conveniently with the filling equipments in the medical industry. In the process of filling the crosslinking active solution into the syringe, the needle connection side of the syringe is usually sealed; the crosslinking active solution is filling from the open end (the push rod side of the syringe), which is then sealed with a rubber plug; and finally the push rod is installed. In the step (3) as described above, the crosslinking active solution filled into the syringe forms the disulfide-bond crosslinked hydrogel. The time taken for the crosslinking active solution to gradually form the disulfide-bond crosslinked hydrogel in the injectable container is generally longer than 30 minutes. Increasing temperature can promote gelation, with the gelation time usually from a few hours to several days. The gelation process can also be accelerated by illumination or electron beam irradiation. The gelation process can also be significantly affected by such factors as pH value of the crosslinking active solution and thiol group content of the biocompatible macromolecule. The higher the pH value of the crosslinking active solution is, the faster the gelation process will be. A pH value of weak acid, neutrality or weak base is usually adopted in the present invention. The increase in the thiol group content of the biocompatible macromolecule will also significantly promote the gelation process.

In the present invention, the concentration of the oxygen dissolved in the crosslinking active solution can also be regulated as required before and after the step (1), so as to regulate the gelation process and the gel property. Concentration of the oxygen dissolved in the crosslinking active solution can be increased or decreased by controlling such parameters as partial pressure of oxygen gas, temperature, and time. Concentration of the oxygen dissolved in the crosslinking active solution can be decreased through vacuum pumping or interaction between the crosslinking active solution and a gas whose oxygen partial pressure is smaller than the oxygen partial pressure in the atmospheric air. Vacuum pumping is the most commonly used method for removing the dissolved oxygen. Keeping the crosslinking active solution under vacuum for a certain period of time can then remove most of the dissolved oxygen; and then filling the crosslinking active solution into the injectable container and sealing it under the protection of the inert gas. Here the disulfide-bond crosslinked hydrogel has a longer gelation time and lower strength. Concentration of the oxygen dissolved in the crosslinking active solution can be increased through interaction between the crosslinking active solution and a gas whose oxygen partial pressure is higher than the oxygen partial pressure in the atmospheric air. Getting in touch with a gas containing oxygen gas is a commonly used method for increasing concentration of the oxygen dissolved in the crosslinking active solution. The gas containing oxygen gas can be selected from pressurized air, pure oxygen gas or other gases containing oxygen gas, where the partial pressure of oxygen gas is higher than that of oxygen gas in the atmospheric air; increasing the partial pressure of oxygen gas can then significantly increase the concentration of the oxygen dissolved in the crosslinking active solution. During the operation process, the gas containing oxygen gas can be directed into the crosslinking active solution or above the solution, with the dissolution speed of oxygen gas increased by stirring. While getting in touch with the gas containing oxygen gas, the crosslinking active solution can be conveniently filled into the syringe, which will be sealed quickly with a rubber plug to prevent the dissolved oxygen from escaping due to variation of the air pressure.

After the crosslinking active solution is filled into the syringe, the rubber plug usually directly reaches the solution surface when the filling and sealing equipment is used to plug, with no space left. However, the depth of the rubber plug in the syringe can also be adjusted flexibly as required, with a certain volume of space left. For example, when filling 5 mL crosslinking active solution into a 10 mL syringe, the plug can be positioned at 6 mL or other scales to get the syringe sealed as required. With the current available syringe prefilling and sealing production equipment, the space in the syringe can conveniently be filled with gas (such as air, and pure oxygen gas etc.), which further regulates concentration of the oxygen dissolved in the crosslinking active solution. Moreover, the crosslinking active solution can also be in contact with the gas containing oxygen gas before being sealed with the rubber plug, which further regulates concentration of the oxygen dissolved in the crosslinking active solution. For example, the gas with a certain partial pressure of oxygen gas is directed into the injectable container, which will be sealed with a rubber plug after a certain period of time. However, this operation makes the process complicated, and is generally not adopted.

On the other hand, the present invention provides the injectable in-situ crosslinked hydrogel prepared by the method as described above.

In the present invention, the biocompatible macromolecule in the crosslinking active solution containing more than two thiol groups on the side chain can be purified in the solution state, and the current available purification processes (e.g. ultrafiltration) can remove impurities completely; besides, without crosslinking agent added in the gelation process, the oxygen gas dissolved in the solution can oxidize the thiol group into the crosslinked disulfide bond, with water as the byproduct. Therefore, compared with other injectable crosslinked gel, the injectable in-situ crosslinked gel prepared by the present invention is significantly advantageous.

On the other hand, the present invention further applies the injectable in-situ crosslinked hydrogel described as above in medicine and surgery.

The medical applications of the in-situ crosslinked hydrogel prepared by the present invention include: as wound dressing for skin or other wounds to expedite wound healing; for preventing adhesion including the fibrous adhesion between tissues or organs after a surgical operation (e.g. sinus surgery); for tissue repair and regeneration such as skin regeneration and cartilage regeneration; and as a joint lubricant for arthritis treatment and so on.

The pharmaceutical applications of the in-situ crosslinked hydrogel prepared by the present invention include being used as a carrier for various active therapeutic substances to realize sustained release. The active therapeutic substance can be an activity factor in chemical drug or biology, such as antiphlogistic, antibiotic, analgesic, anaesthetic, wound healing enhancer, cell growth promoter or inhibitor, immune stimulant, and antiviral medicine.

DETAILED DESCRIPTION

The following examples can make those skilled in the art understand the present invention more completely, rather than limit the present invention in any way.

Example 1

Preparation of Thiolated Sodium Hyaluronate

The thiolated sodium hyaluronate was prepared by the method disclosed by Shu et al in *Biomacromolecules*, 3, 1304, 2002. 20 g hyaluronic acid was dissolved in 2 L distilled water. 23.8 g dithio dipropyl dihydrazide was added and stirred to dissolve. Then pH value of the solution was adjusted to 4.75 with 0.1 mol/L hydrochloric acid solution. 19.2 g 1-ethyl-3-(3-dimethylaminepropyl) carbodiimide hydrochloride (Aldrich, the United States) was added and stirred electromagnetically. An appropriate amount of 0.1 mol/L hydrochloric acid solution was continuously added into the above solution to keep the solution pH value at 4.75. 1.0 mol/L sodium hydroxide was added to adjust the pH value to 7.0 to terminate the reaction. 100 g dithioerythritol (Diagnostic Chemical Limited, the United States) and an appropriate amount of 1.0 mol/L sodium hydroxide were added under stirring. The pH value of the solution was adjusted to 8.5 and reaction was conducted at room temperature under electromagnetic stirring for 24 hours. Then 1 mol/L hydrochloric acid was added into the above solution until pH was about 3.5. The above solution was filled into a dialysis tube (cut-off molecular weight 3500, Sigma, the United States), and dialysized against large amount 0.0003 mol/L hydrochloric acid and 0.1 mol/L sodium chloride solution for 5 days, with the change of dialysis solution every 8 hours; and then further dialysized against large amount of 0.0003 mol/1 hydrochloric acid solution for 3 days, with the change of dialysis solution every 8 hours. Finally the solution in the dialysis tube was collected and lyophilized to give white flocculent solid.

The above white flocculent solid was dissolved in distilled water to give the 1.0-2.5% w/v solution and the solution pH value was adjusted to to 4.0-8.0. After sterilized by filtration, the solution was immediately used or stored under frozen for future use. Or during the preparation process as described above, the purified solution by dialysising was concentrated through dialysis column to appropriate concentration (usually 1.0-2.5% w/v), and the pH value of the solution was adjusted (usually 4.0-8.5). After sterilized by filtration, the solution was used immediately or stored under frozen for future use.

The degree of substitution of the side chain thiol group in the thiolated sodium hyaluronate was 42/100 disaccharide repeated units detected by the hydrogen spectrum nuclear magnetic resonance ($^1$H-NMR) (with $D_2O$ as the solvent); and the molecular weight and its polydispersity (determined by GPC) are as below: the weight-average molecular weight 136,000, and the number-average molecular weight 61,000.

Example 2

Synthesis and Characterization of Thiolated Chondroitin Sulfate 1 g chondroitin sulfate (Type c, from the shark cartilage, Sigma, the United States) was dissolved in 100 mL distilled water to give a clear transparent solution. 0.704 g disuccinate bisacylcystamine dihydrazide was added into the above solution (Shu et al, Chinese invention patent No. CN101190891), and stirred to dissolve. The pH value of the solution was adjusted to 4.75 with 0.1 mol/L hydrochloric acid solution. Then 0.192 g 1-ethyl-3-(3-dimethylaminepropyl) carbodiimide hydrochloride (Aldrich, the United States) was added under electromagnetic stirring. An appropriated amount of 0.1 mol/L hydrochloric acid solution was added continuously into the above solution to keep the solution pH value at 4.75, The solution was stirred electromagnetically at room temperature for 2 hours. Then 10 g dithioerythritol (Diagnostic Chemical Limited, the United States) and a small amount of 0.1 mol/L sodium hydroxide solution were added under electromagnetic stirring. The gel was dissolved gradually; 0.1 mol/L sodium hydroxide solution was added continuously at the same time to keep the solution pH value at 8.5. After all the gel was dissolved, the solution was stirred electromagnetically at room temperature for 24 hours. Then 6 mol/L hydrochloric acid solution was added into the above solution until pH was about 3.0. The above solution was filled into a dialysis tube (cut-off molecular weight 2000, Sigma, the United States), and dialysized against 10 L 0.001 mol/L hydrochloric acid and 0.3 mol/L sodium chloride solution for 5 days, with the change of dialysis solution every 8 hours; and then further dialysized against 10 L 0.001 mol/L hydrochloric acid solution for 3 days with the change of dialysis solution every 8 hours. Finally the solution in the dialysis tube was lyophilized or dehydrated through dialysis column to appropriate concentration (3.0-6.0% w/v), and pH value of the solution was adjusted (usually 4.0-8.5). The solution was sterilized by filtration and stored for future use.

The characteristic methyl absorption peak of the acetyl group of chondroitin sulfate was used as the internal standard. The substitution degree of the side chain of thiolated chondroitin sulfate was calculated out according to area of the absorption peak, with the result being 47%.

The molecular weight and its polydispersity were detected by the GPC: The weight-average molecular weight 38,000, the number-average molecular weight 17,000, and the molecular weight polydispersity 2.23.

By the modified Ellman method reported by Shu et al in *Biomacromolecules*, 3, 1304, 2002, content of the active thiol group of thiolated chondroitin sulfate was detected: 44.2 thiol groups/100 chondroitin sulfate disaccharide repeated units.

Example 3

Preparation of Thiolated Gelatin 1 g gelatin (Type B, from pig skin, Sigma, the United States) was dissolved in 100 mL distilled water to give a clear transparent solution. 0.75 g disuccinate bisacylcystamine dihydrazide was added into the above solution and stirred to dissolve. The pH value of the solution was adjusted to 4.75 with 0.1 mol/L hydrochloric acid solution. 1 g 1-ethyl-3-(3-dimethylaminepropyl) carbodiimide hydrochloride (Aldrich, the United States) was added under electromagnetic stirring. An appropriate amount of 0.1 mol/L hydrochloric acid solution was continuously added into the above solution to keep the solution pH value at 4.75. The solution was increased in viscosity continuously, and gel was formed in about 10 minutes. After the gel was formed, the solution was kept still at room temperature for 2 hours. Then 10 g dithioerythritol (Diagnostic Chemical Limited, the United States) and a small amount of 0.1 mol/L sodium hydroxide solution were added under stirring. The gel was dissolved gradually; 0.1 mol/L sodium hydroxide solution was continuously at the same time to keep the solution pH value at 8.5. After all the gel was dissolved, the reaction was conducted at room temperature under electromagnetical stirring for 24 hours. Then 6 mol/L hydrochloric acid solution was added into the above solution until pH was about 3.0. The above solution was filled into a dialysis tube (cut-off molecular weight 2000, Sigma, the United States), and dialysized against 10 L 0.001 mol/L hydrochloric acid and 0.3 mol/L sodium chloride solution for 5 days, with the change of dialysis solution every 8 hours; and then further dialysized against 10 L 0.001 mol/L hydrochloric acid solution for 3 days with the change of dialysis solution every 8 hours. Finally the solution in the dialysis tube was collected and lyophilized to give about 0.6 g of white flocculent solid.

The white flocculent solid as described above was dissolved in distilled water to give the 3.0-6.0% w/v solution, and pH value of the solution was 4.0-8.0. After sterilized by filtration, the solution was used immediately or stored under frozen for future use.

Small molecular impurity peaks were not detected by the GPC (with pure water as the mobile phase, and detected at UV 210 nm), indicating that the synthetic thiolated gelatin is highly purified and the impurities were below the least limitation of equipment.

Content of the active thiol group of thiolated gelatin was 0.57 mmol/g detected by the modified Ellman method reported by Shu et al in *Biomacromolecules*, 3, 1304, 2002.

Example 4

Preparation of Injectable In-Situ Crosslinked Hydrogel

Sodium Hyaluronate Gel:

The thiolated sodium hyaluronate solution prepared in Example 1 (pH 7.0, 1.0% w/v) was filled into a 1 mL syringe immediately after sterilization by filtration, was sealed and kept at room temperature. It was observed after one week that the solution sealed in the syringe had lost fluidity to form a gel. The gel was insoluble in water, but soluble in the dithioerythreitol solution, confirming the formation the crosslinked disulfide bond.

Chondroitin Sulfate Gel:

The thiolated chondroitin sulfate solution prepared in Example 2 (pH 7.0, 5.0% w/v) was filled into a 1 mL syringe immediately after sterilization by filtration. The syringe was sealed and kept at room temperature. It was observed after one week that the solution sealed in the syringe had lost fluidity to form a gel. The gel was insoluble in water, but soluble in the dithioerythreitol solution, confirming the formation of crosslinked disulfide bond.

Gelatin Gel:

The thiolated gelatin solution prepared in Example 3 (pH 7.0, 5.0% w/v) was filled into a 1 mL syringe immediately after aseptic filtration, and sealed to kept at room temperature. It was found after one week that the solution sealed in the syringe had lost fluidity to form the gel. The gel was insoluble in water, but soluble in the dithioerythreitol solution, confirming the formation of crosslinked disulfide bond.

Example 5

Preparation of Injectable In-Situ Crosslinked Hydrogel

Sodium Hyaluronate/Gelatin Gel:

The thiolated sodium hyaluronate solution prepared in Example 1 (pH 7.0, 1.0% w/v) and the thiolated gelatin solution prepared in Example 3 (pH 7.0, 5.0% w/v) were mixed uniformly according to an appropriate volume ratio (e.g. 10:1, 1:1 and 1:10), and the mixed solution was filled into a 1 mL syringe which was then sealed and kept at room temperature. It was observed after one week that the solution sealed in the syringe had lost fluidity to form a gel. The gel was insoluble in water, but soluble in the dithioerythreitol solution, confirming the formation of the crosslinked disulfide bond.

Chondroitin Sulfate/Gelatin Gel:

The thiolated chondroitin sulfate solution prepared in Example 2 (pH 7.0, 5.0% w/v) and the thiolated gelatine solution prepared in Example 3 (pH 7.0, 5.0% w/v) were mixed uniformly according to an appropriate volume ratio (e.g. 10:1, 1:1 and 1:10), and the mixed solution was immediately filled into a 1 mL syringe which was then sealed and kept at room temperature. It was observed after one week that the solution sealed in the syringe had lost fluidity to form a gel. The gel was insoluble in water, but soluble in the dithioerythreitol solution, confirming the formation of the crosslinked disulfide bond.

Sodium Hyaluronate/Chondroitin Sulfate/Gelatin Gel:

The thiolated sodium hyaluronate solution prepared in Example 1 (pH 7.0, 1.0% w/v), the thiolated chondroitin sulfate solution prepared in Example 2 (pH 7.0, 5.0% w/v), and the thiolated gelatin solution prepared in Example 3 (pH 7.0, 5.0% w/v) were mixed uniformly according to an appropriate volume ratio (e.g. 1:1:1), and the mixed solution was immediately filled into a 1 mL syringe which was then sealed and kept at room temperature. It was observed after one week that the solution sealed in the syringe has lost fluidity to form a gel. The gel was insoluble in water, but soluble in the dithioerythreitol solution, confirming the formation of the crosslinked disulfide bond.

Example 6

Preparation of Injectable In-Situ Crosslinked Hydrogel

Sodium Hyaluronate Gel Containing Chondroitin Sulfate:

Chondroitin sulfate (Type c, from shark cartilage, Sigma, the United States) was dissolved in water to give the 1.0% w/v solution. It was mixed with the thiolated sodium hyaluronate solution prepared in Example 1 (pH 7.0, 1.5% w/v) according to the volume ratio of 2:1, then the mixed solution was immediately filled into a 1 mL syringe which was then sealed and kept at room temperature. It was observed after one week that the solution sealed in the syringe has lost fluidity to form a gel. The gel was insoluble in water, but soluble in the dithioerythreitol solution, confirming the formation of the crosslinked disulfide bond.

Chondroitin Sulfate Gel Containing Sodium Hyaluronate:

Sodium hyaluronate (with the molecular weight about 1,000,000, manufactured by Shandong Freda Biochem Co., Ltd.) was dissolved in water to give the 1.0% w/v solution. It was mixed uniformly with the thiolated chondroitin sulfate solution prepared in Example 2 (pH 7.0, 6.0% w/v), then the mixed solution was immediately filled into a 1 mL syringe which was then sealed and kept at room temperature. It was observed after one week that the solution sealed in the syringe had lost fluidity to form a gel. The gel was insoluble in water, but soluble in the dithioerythreitol solution, confirming the formation of the crosslinked disulfide bond.

Gelatin Gel Containing Sodium Hyaluronate:

Sodium hyaluronate (with the molecular weight about 1,000,000, manufactured by Shandong Freda Biochem Co., Ltd.) was dissolved in 0.9% physiological saline to give the 1.0% w/v solution. It was mixed uniformly with the thiolated gelatin solution prepared in Example 3 (pH 7.0, 8.0% w/v). The mixed solution was immediately filled into a 1 mL syringe, which was then sealed and kept at room temperature. It was observed after one week that the solution sealed in the injector had lost fluidity to form a gel. The gel is insoluble in water, but soluble in the dithioerythreitol solution containing sodium chloride, confirming the formation of the crosslinked disulfide bond.

Example 7

Regulation of Concentration of Oxygen Dissolved in Active Crosslinking Solution The thiolated sodium hyaluronate solution prepared in Example 1 (pH 8.0, 1.0% w/v) was evacuated for 10 minutes and then exposed to air at room temperature under electromagnetic stirring. Concentration of the oxygen dissolved in the solution was recorded by a dissolved oxygen analyzer (HI 9143, manufactured by the HANNA company) at a certain time interval, with the measuring results as below:

| Time (minutes) | 0 | 5 | 10 | 15 | 20 | 25 | 30 | 35 |
|---|---|---|---|---|---|---|---|---|
| Concentration of Dissolved Oxygen (mg/L) | 0.28 | 2.77 | 4.73 | 5.82 | 6.50 | 7.00 | 7.22 | 7.33 |

Example 8

Preparation and Characterization of Injectable In-Situ Crosslinked Hydrogel

In Example 7, the solution stirred at room temperature for 5 minutes (solution A) and the other solution stirred at room temperature for 20 minutes (solution B) was filled into a 1 mL syringe, respectively, and the syringes were sealed and kept at room temperature. It was observed after 48 hours that the solution A, though having become very viscous, still had certain fluidity; while the solution B had lost fluidity completely and formed a gel. Through measuring content of the disulfide bond in the solutions A and B with the method reported by Shu et al in *Biomacromolecules*, 3, 1304, 2002, it was found that content of the disulfide bond in the solution B was about 15% higher than that in the solution A.

Example 9

Regulation of Concentration of Oxygen Dissolved in Active Crosslinking Solution The thiolated sodium hyaluronate solution prepared in Example 1 (pH 8.0, 1.0% w/v) was exposed to 1 atm oxygen gas in a sealed container under electromagnetic stirring. Concentration of the oxygen dissolved in the solution was recorded by a dissolved oxygen analyzer (HI 9143, manufactured by the HANNA company) at a certain time interval, with the measuring results as below:

| Time (minute) | 0 | 5 | 10 | 15 | 20 |
|---|---|---|---|---|---|
| Concentration of Dissolved Oxygen (mg/L) | 7.38 | 13.92 | 18.73 | 24.82 | 28.50 |

Example 10

Preparation and Characterization of Injectable In-Situ Crosslinked Hydrogel

In Example 9, when exposing to 1 atm oxygen gas, the solution stirred for 0 minute (solution A) and the solution stirred for 10 minutes (solution B) were filled into a 1 mL syringe, respectively. The syringe were sealed and kept at room temperature. In the solution B, gel was formed within 24 hours, while gelation of the solution A took about 48 hours. After 48 hours, it was found that content of the disulfide bond in the solution B was about 30% higher than that in the solution A by measuring content of the disulfide bond in the solutions A and B with the method reported by Shu et al in *Biomacromolecules*, 3, 1304, 2002.

Example 11

Preparation of Injectable In-Situ Crosslinked Hydrogel Containing Drug

Into the 10 mL thiolated sodium hyaluronate solution prepared in Example 1 (pH 7.0, 1.0% w/v), 50 mg antibiotics (gentamicin), 100 mg antitumor drug (Taxol) or 50 μg basic growth factor was added, alternatively. The solution was mixed uniformly and then immediately filled into a 1 mL syringe. The syringe was sealed and kept at room temperature. It was observed after one week that the solution sealed in the syringe had lost fluidity to form a gel.

Example 12

Preparation and Characterization of Injectable In-Situ Crosslinked Hydrogel Containing Corticosteroid Into the 10 mL thiolated sodium hyaluronate solution prepared in Example 1 (pH 7.0, 1.0% w/v), 0.1-10 mg one type of corticosteroid (e.g. Beclomethasone, Beclomethasone dipropionate, Budesonide; Dexamethasone, Prednisolone or Prednisone) was added. The solution was mix uniformly and immediately filled into a 1 mL syringe which was then sealed and kept at room temperature. It was observed after one week that the solution sealed in the syringe had lost fluidity to form a gel.

0.2 mL gel containing drug as described above was filled into a 15 mL plastic centrifugal tube; 10 mL phosphate buffer solution was added into the centrifugal tube which was then put in an incubator (37° C., 100 rpm); ultraviolet absorption of the drug in the supernatant was recorded at a certain time interval. The measured wavelength results are displayed as below: Beclomethasone 246 nm; Beclomethasone dipropionate 240 nm; Budesonide 248 nm; Dexamethasone 242 nm; Prednisolone 248 nm; and Prednisone 244 nm.

The cumulative releasing percentages of the drug at different times are as below:

| Time (day) | Beclomethasone | Beclomethasone dipropionate | Budesonide | Dexamethasone | Prednisolone | Prednisone |
|---|---|---|---|---|---|---|
| 7 | 61% | <1% | 21% | 39% | 95% | 82% |
| 14 | 82% | <1% | 40% | 61% | 100% | 95% |
| 21 | 91% | <1% | 57% | 74% | 100% | 100% |

It can be seen from the above results that the injectable in-situ crosslinked hydrogel, as a sustained release carrier for many drugs, has good sustained release effect for six kinds of corticosteroid. Due to differences in hydrophobicity, the drugs are very different in their behaviors of being released from the gel. The stronger the hydrophobicity of the drug is, the more sustained the release is. Taking the more hydrophilic Prednisolone for example, it had be released substantially completely in 7 days; while for the very hydrophobic Beclomethasone dipropionate, release was rarely detected.

Example 13

Application of Injectable In-Situ Crosslinked Hydrogel to Prevent Restenosis of Nasal Sinus Ostium After Nasosinusitis Surgery Eight New Zealand white male rabbits after Pasteur sterilization were used, each weighing 3.5-4.0 kg; they were anesthetized by injecting ketamine (35 mg/kg) and toluolzosin (5 mg/kg) into their muscles. After external backsides were stripped off their noses, the rabbits were disinfected with iodine, and anesthetized with a 3 mL mixed liquid of 1% lidocaine and 1:100000 adrenaline. Under aseptic conditions, a 2.5 mm perpendicular incision along the midline was made. Soft tissues and periosteum covering on the antrum were lifted and separated. Anterior wall of the antrum was opened with a surgery electric drill, breaking through between middle wall of the antrum and the nasal cavity with a 4 mm spherical cutting drill, thus forming a cylindrical pore canal of 4 mm in diameter without mucosa on the edge. Both sides of the pore canal of the four rabbits were filled with the sodium hyaluronate gel prepared in Example 4 (therapeutic group), and both sides of the pore canal of the other four rabbits were filled with nothing (control group). Then the periosteum was sewed up with an absorbable ligature, and the antrum was sewed up and sealed with skin by the absorbable ligature. No need for any other bandage. Routine diet and water were offered to the animals after the operation.

The rabbits were sacrificed two weeks later. The healed wound was incised after the sacrifice to expose the sinus cavity. Flushing with water and meanwhile gently extracting residues from the sinus cavity with an extractor, and inspecting medial wall of the nasal sinus with a 30-degree nasal endoscope and photographing it. Each of the ostium was measured with a ruler with millimeter scale. The ostium was observed and measured by means of the double-blind technique. The ostium measuring results of the therapeutic group and the control group are as below:

|  | Therapeutic group | Control group |
| --- | --- | --- |
| Diameter of nasal sinus ostium (mm) | 2.9 ± 1.32 | 0.7 ± 0.44 |

Restenosis of the nasal sinus ostium, as an important problem with the nasosinusitis clinical operation, may affect the operation effect, and even cause the nasosinusitis relapse. The results as described above indicate that the injectable in-situ crosslinked hydrogel can significantly prevent stenosis of the nasal sinus ostium, and is thus hopeful to get widely used in the clinical practice.

Example 14

Promoting Wound Healing with Injectable In-Situ Crosslinked Hydrogel

Adopted animal model reported by Kicker et al in *Biosubstances*, 23, 3661, 2002 was briefly described as below: After ten mice each weighing 25 g were anaesthetized, epidermis and dermis on the back of the mice were excised with a scalpel, with a wound of 1 cm in diameter obtained. The wound of the therapeutic group was filled with 0.3 mL sodium hyaluronate gel prepared in Example 4, then bandaged with the Tegaderm™ excipients and gauze; the wound of the control group was directly bandaged with the Tegaderm™ excipients and gauze. The mice were sacrificed 5 and 10 days after the operation, and the wound healing situation was characterized with the epidermis regeneration rate (percentage of the neoepidermis to the initial wound). Results of the epidermis regeneration rate (%) are as below:

| Time (day) | 5 | 10 |
| --- | --- | --- |
| Control group | 47 ± 15 | 79 ± 13 |
| Therapeutic group | 80 ± 13 | 95 ± 10 |

The injectable in-situ crosslinked hydrogel significantly promotes epidermis regeneration of the wound, and can thus be used as wound dressing in the clinic practice.

The present invention realizes the gelation process of oxidizing the thiol group into the disulfide bond by the oxygen dissolved in the crosslinking active solution. This method eliminates the technical prejudice that being open to air is required for preparing the disulfide-bond crosslinked gel, and resolves the technical problem with the large-scale industrialized production; besides, this method can flexibly regulate concentration of the oxygen dissolved in the crosslinking active solution by conveniently controlling such parameters as temperature and partial pressure of oxygen gas etc., thus regulating the disulfide bond crosslinking process and property of the disulfide-bond crosslinked hydrogel; meanwhile the gelation process is completed in an injectable container and the produced hydrogel is injectable. The method of the present invention has many advantages, such as no need for crosslinking agent, simple preparation process, convenient application, containing no impurities, good biocompatibility, no toxic and side effect, and wide application in medical science.

The present invention, with the gelation process completed in an injectable container, further has such advantages as avoiding secondary pollution, being extremely convenient for clinical application, no cross infection during usage, preventing unclean air from getting in touch with the product in a sickroom, no need for extracting medicine, and being disposable.

What is claimed is:
1. A method of preparing an injectable in-situ crosslinked hydrogel, comprising:
   (1) filling a crosslinking active solution into an injectable container, wherein the crosslinking active solution contains at least one biocompatible macromolecule with more than two thiol groups on side chains;
   (2) sealing the injectable container containing the crosslinking active solution; and

(3) oxidizing the thiol groups into disulfide bonds to form the crosslinked hydrogel by oxygen dissolved in the crosslinking active solution in the sealed injectable container;

wherein, crosslinking occurs in-situ in the sealed injectable container; and wherein, the time taken for the crosslinking active solution to gradually form a disulfide-bond crosslinked hydrogel in the injectable container is longer than 30 minutes.

2. The method of preparing the injectable in-situ crosslinked hydrogel according to claim 1, wherein the concentration of the oxygen dissolved in the crosslinking active solution is regulated before and after the step (1).

3. The method of preparing the injectable in-situ crosslinked hydrogel according to claim 2, wherein regulation of the concentration of the oxygen dissolved in the crosslinking active solution refers to increasing or decreasing the concentration of the dissolved oxygen.

4. The method of preparing the injectable in-situ crosslinked hydrogel according to claim 2, wherein the concentration of the oxygen dissolved in the crosslinking active solution can be controlled by regulating temperature, oxygen partial pressure of a gas in contact with the crosslinking active solution, or contact time.

5. The method of preparing the injectable in-situ crosslinked hydrogel according to claim 3, wherein the method of increasing the concentration of the dissolved oxygen includes interacting the crosslinking active solution with a gas whose oxygen partial pressure is higher than that in atmospheric air.

6. The method of preparing the injectable in-situ crosslinked hydrogel according to claim 3, wherein the method of decreasing the concentration of the dissolved oxygen includes evacuating and exposing the crosslinking active solution to the gas whose the oxygen partial pressure is lower than that in the atmospheric air.

7. The preparation method of preparing the injectable in-situ crosslinked hydrogel according to claim 1, wherein the injectable container is a syringe or an extrusible container.

8. The method of preparing the injectable in-situ crosslinked hydrogel according to claim 1, wherein the biocompatible macromolecule with more than two thiol groups on the side chain is a derivative of polysaccharides, proteins or synthetic macromolecules produced by one or more chemical modifications, wherein at least one of the chemical modifications is thiol modification.

9. The method of preparing the injectable in-situ crosslinked hydrogel according to claim 8, wherein the polysaccharide is selected from chondroitin sulfate, heparin, heparan, alginic acid, hyaluronic acid, dermatan, dermatan sulfate, pectin, carboxymethyl cellulose, and chitosan, as well as their salt forms; the protein is selected from collagen, acidic gelatin, alkaline gelatin, and gene recombination gelatin; and the synthetic macromolecule is selected from polyacrylic acid, polyaspartic acid, polytartaric acid, polyglutamic acid, and polyfumaric acid, as well as their salt forms.

10. The method of preparing the injectable in-situ crosslinked hydrogel according to claim 8, wherein the thiol modification includes the following chemical reaction processes: reacting of carboxyl groups with diamines or dihydrazides containing the disulfide bonds under activation of carbodiimide to produce intermediate products, then reducing the disulfide bonds into the thiol groups, and purifying the thiolated derivatives.

11. The method of preparing the injectable in-situ crosslinked hydrogel according to claim 8, wherein the biocompatible macromolecules containing more than two thiol groups on the side chain are selected from the following group: thiolated sodium hyaluronate derivatives containing more than two thiol groups on the side chain, thiolated chondroitin sulfate derivatives containing more than two thiol groups on the side chain, thiolated gelatine derivatives containing more than two thiol groups on the side chain, thiolated collagen derivatives containing more than two thiol groups on the side chain, thiolated chitosan derivatives containing more than two thiol groups on the side chain, or thiolated heparin derivatives containing more than two thiol groups on the side chain.

12. The method of preparing the injectable in-situ crosslinked hydrogel according to claim 1, wherein the crosslinking active solution contains two or more biocompatible macromolecules containing more than two thiol groups on the side chain.

13. The method of preparing the injectable in-situ crosslinked hydrogel according to claim 12, wherein the crosslinking active solution contains two or more thiolated derivatives selected from the following group: the thiolated sodium hyaluronate derivatives, the thiolated chondroitin sulfate derivatives, the thiolated heparin derivatives, the thiolated gelatine derivatives, the thiolated collagen derivatives, and the thiolated chitosan derivatives.

14. The method of preparing the injectable in-situ crosslinked hydrogel according to claim 1, wherein the crosslinking active solution further contains one or more polysaccharides, proteins and synthetic macromolecules.

15. The method of preparing the injectable in-situ crosslinked hydrogel according to claim 14, wherein the polysaccharide is selected from chondroitin sulfate, heparin, heparan, alginic acid, hyaluronic acid, dermatan, dermatan sulfate, pectin, carboxymethyl cellulose, and chitosan, as well as their salt forms; the protein is selected from collagen, acidic gelatin, alkaline gelatin, and gene recombination gelatin; and the synthetic macromolecule is selected from polyacrylic acid, polyaspartic acid, polytartaric acid, polyglutamic acid, and polyfumaric acid, as well as their salt forms.

16. The method of preparing the injectable in-situ crosslinked hydrogel according to claim 1, wherein the crosslinking active solution contains an active drug component.

17. The method of preparing the injectable in-situ crosslinked hydrogel according to claim 14, wherein the crosslinking active solution contains an active drug component.

18. The method of preparing the injectable in-situ crosslinked hydrogel according to claim 16, wherein the active drug component can be either dispensed in the crosslinking active solution in a solid particle form, or dissolved in the crosslinking active solution.

19. The method of preparing the injectable in-situ crosslinked hydrogel according to claim 17, wherein the active drug component can be either dispersed in the crosslinking active solution in a solid particle form, or dissolved in the crosslinking active solution.

20. The method of preparing the injectable in-situ crosslinked hydrogel according to claim 17, wherein the active drug component includes steroids, antibiotics or antitumor drugs.

21. The method of preparing the injectable in-situ crosslinked hydrogel according to claim 16, wherein the active drug component includes steroids, antibiotics or antitumor drugs.

* * * * *